US008366677B2

(12) United States Patent
Kaspar et al.

(10) Patent No.: US 8,366,677 B2
(45) Date of Patent: Feb. 5, 2013

(54) MICRONEEDLE ARRAYS FORMED FROM POLYMER FILMS

(75) Inventors: Roger L. Kaspar, Santa Crus, CA (US); Tycho Speaker, Santa Cruz, CA (US)

(73) Assignee: Transderm, Inc., Santa Cruz, CA (US)

( * ) Notice: Subject to any disclaimer, the term of this patent is extended or adjusted under 35 U.S.C. 154(b) by 0 days.

(21) Appl. No.: 12/187,268

(22) Filed: Aug. 6, 2008

(65) Prior Publication Data
US 2009/0043279 A1 Feb. 12, 2009

Related U.S. Application Data

(60) Provisional application No. 60/963,725, filed on Aug. 6, 2007, provisional application No. 60/994,568, filed on Sep. 19, 2007.

(51) Int. Cl.
*A61M 5/00* (2006.01)
*A61M 5/32* (2006.01)
*A61M 25/00* (2006.01)
*B29D 7/00* (2006.01)

(52) U.S. Cl. ........ 604/173; 604/174; 604/264; 604/272; 264/159

(58) Field of Classification Search .................. 604/272, 604/506, 173, 501, 21, 174, 264, 117; 264/159
See application file for complete search history.

(56) References Cited

U.S. PATENT DOCUMENTS

| 6,334,856 | B1 | 1/2002 | Allen et al. | |
|---|---|---|---|---|
| 6,503,231 | B1 | 1/2003 | Prausnitz et al. | |
| 6,537,264 | B1 * | 3/2003 | Cormier et al. | 604/506 |
| 6,611,707 | B1 | 8/2003 | Prausnitz et al. | |
| 6,689,100 | B2 * | 2/2004 | Connelly et al. | 604/117 |
| 6,743,211 | B1 | 6/2004 | Prausnitz et al. | |
| 7,226,439 | B2 | 6/2007 | Prausnitz et al. | |
| 7,416,541 | B2 | 8/2008 | Yuzhakov et al. | |
| 2002/0111600 | A1 * | 8/2002 | Cormier et al. | 604/506 |
| 2002/0138049 | A1 * | 9/2002 | Allen et al. | 604/272 |
| 2004/0049150 | A1 | 3/2004 | Dalton et al. | |
| 2005/0209565 | A1 * | 9/2005 | Yuzhakov et al. | 604/173 |
| 2007/0049901 | A1 * | 3/2007 | Wu et al. | 604/506 |
| 2008/0009811 | A1 * | 1/2008 | Cantor | 604/272 |
| 2008/0125743 | A1 * | 5/2008 | Yuzhakov | 604/506 |
| 2008/0269666 | A1 * | 10/2008 | Wang et al. | 604/21 |
| 2008/0269685 | A1 * | 10/2008 | Singh et al. | 604/173 |
| 2009/0099502 | A1 * | 4/2009 | Tokumoto et al. | 604/21 |
| 2009/0131905 | A1 | 5/2009 | Allen et al. | |

FOREIGN PATENT DOCUMENTS

| EP | 1632263 | 3/2008 |
|---|---|---|
| KR | 10-2007-0018410 | 2/2007 |
| WO | WO 99/64580 | 12/1999 |
| WO | WO 00/44438 | 8/2000 |

(Continued)

OTHER PUBLICATIONS

Mark R. Prausnitz. 'Microneedles for transdermal drug delivery.' Advanced Drug Delivery Reviews. 2004, vol. 56, pp. 581-587.

(Continued)

*Primary Examiner* — Kevin C Sirmons
*Assistant Examiner* — Bradley G Thomas, Jr.
(74) *Attorney, Agent, or Firm* — Thorpe North & Western LLP

(57) ABSTRACT

The present invention provides for transdermal delivery devices having microneedle arrays, as well as methods for their manufacture and use. In one embodiment, a transdermal delivery device is provided. The transdermal delivery device includes a polymer layer which has microneedles projecting from one of its surfaces. The microneedles are compositionally homogenous with the polymer base layer.

7 Claims, 10 Drawing Sheets

FOREIGN PATENT DOCUMENTS

| WO | WO 02/064193 | 8/2002 |
| WO | WO 2006/077742 | 7/2006 |
| WO | WO 2006/131931 | 12/2006 |
| WO | WO2008/010681 | 1/2008 |

OTHER PUBLICATIONS

Michel Cormier, et al., 'Transdermal delivery of desmopressin using a coated microneedle array patch system', Journal of Controlled Release, 2004, vol. 97, pp. 503-511.

Schmid; Microneedles May Take the Ouch Out of Flue Shots, Researchers Developing Skin Patch for Influenza Vaccine; msnbc.com; http://www.msnbc.msn.com/id/38301183/from/toolbar; Jul. 18, 2010.

Gonzalez-Gonzalez et al.; Silencing of Reporter Gene Expression in Skin Using siRNAs Delivered by a Soluble Protrusion Array Device(PAD); Molecular Therapy; Sep. 2010; pp. 167-1674; vol. 18.

Related Matter: U.S. Appl. No. 13/157,198, filed Jun. 9, 2011; Roger L. Kaspar.

\* cited by examiner

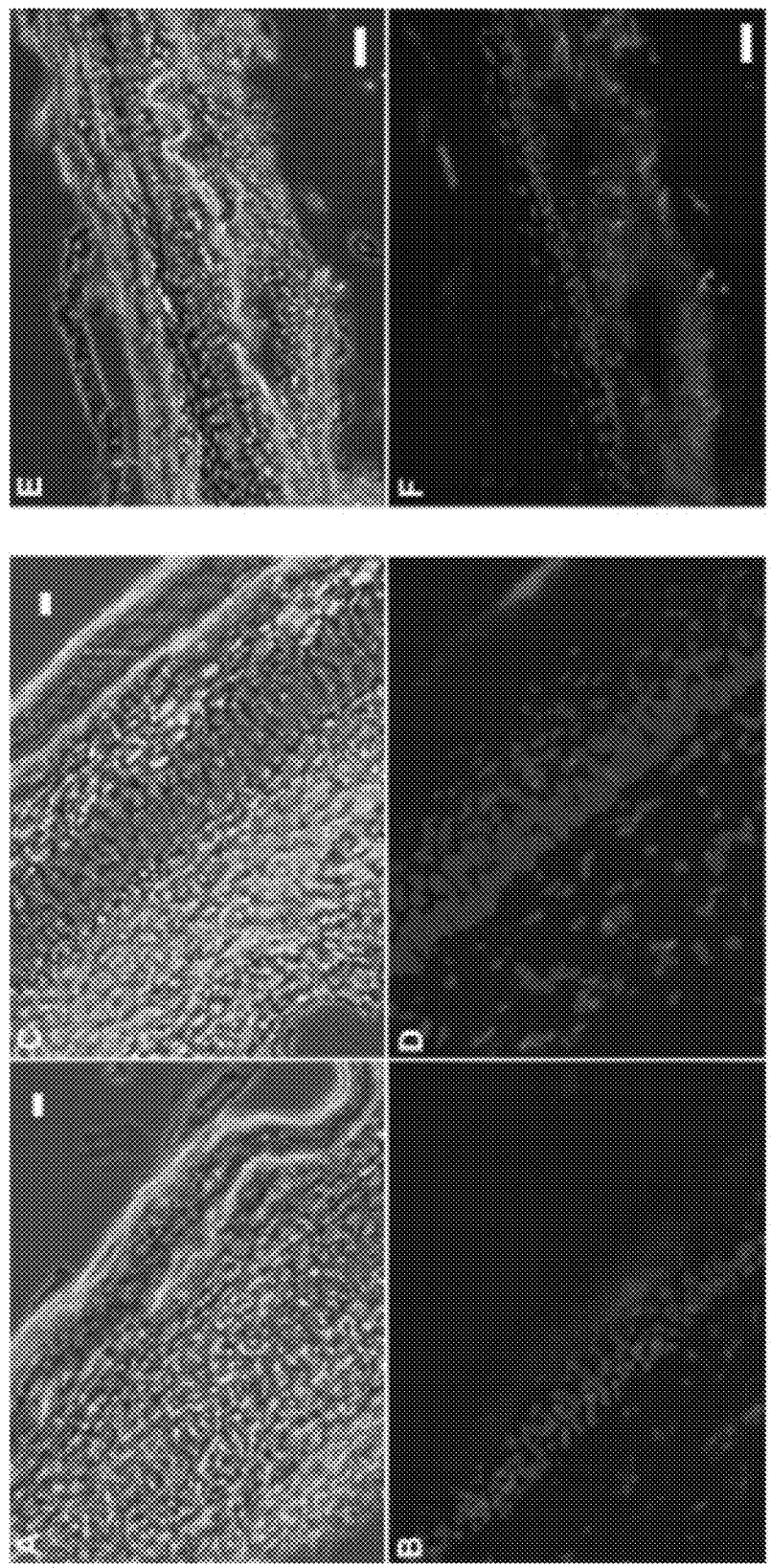
FIG. 5A-F

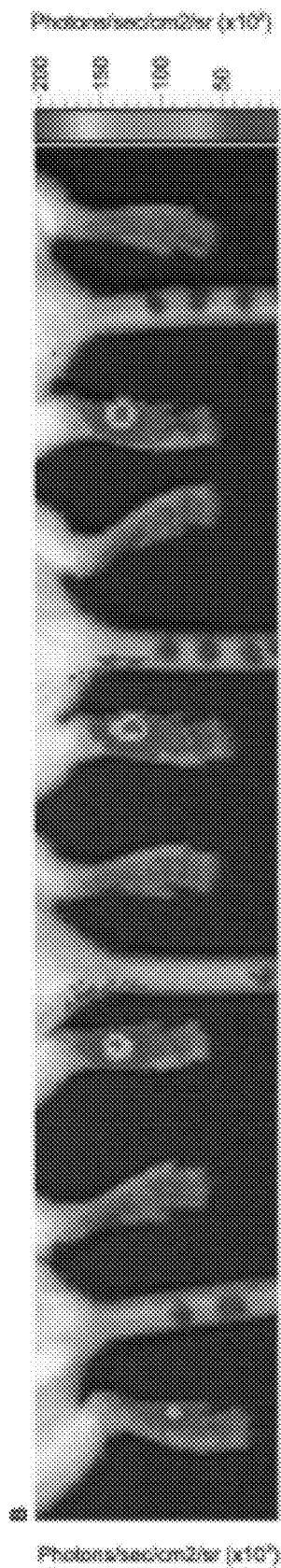

MICRONEEDLE ARRAYS FORMED FROM POLYMER FILMS

This application claims the benefit of U.S. Provisional Application Ser. Nos. 60/963,725, filed Aug. 6, 2007, and 60/994,568, filed Sep. 19, 2007, each of which is incorporated herein by reference.

BACKGROUND

This invention relates generally to the field of devices for the transport of therapeutic or biological molecules into and across skin tissue barriers, such as for drug delivery.

Drugs are commonly administered today through either the oral, parenteral, or transdermal routes of administration. One great challenge to transdermal administration is poor permeation of the active agent through the skin. The rate of diffusion depends in part on the size and hydrophilicity of the drug molecules and the concentration gradient across the stratum corneum. Few drugs have the necessary physiochemical properties to be effectively delivered through the skin by passive diffusion, iontophoresis, electroporation, ultrasound, chemical permeation enhancers, and heat (so-called active systems) have been used in an attempt to improve the rate of delivery. Furthermore, the combination of the active agent, permeation enhancers, and certain carriers have been used in order to try and achieve specific delivery profiles over a desired duration.

SUMMARY OF THE INVENTION

Accordingly, the present invention provides for transdermal delivery devices as well as methods for their manufacture and use. In one embodiment, a transdermal delivery device is provided. The transdermal delivery device includes a polymer layer which has microneedles projecting from one of its surfaces. The microneedles are compositionally homogenous with the polymer base layer.

In another embodiment, a method for administering an active agent transdermally is provided. First a transdermal delivery device is provided. The transdermal device includes a polymer base layer having microneedles projecting from one of its surfaces. The microneedles are compositionally homogenous with the base polymer layer. An active agent is also included in the transdermal delivery device. The transdermal delivery device is applied to a skin surface of a subject in order to deliver the active agent to the subject.

In yet another embodiment, a method of manufacturing a transdermal drug delivery device having a microneedle array is provided. The method involves providing a substrate and then applying a polymer solution to the substrate to form a base layer. An exposed surface of the base layer is then disposed with a textured surface or template having elevated points protruding therefrom such that the elevated points contact the exposed surface of the base layer. Exemplary textured surfaces include but are not limited to arrays of metal pins or points as commonly used in electronics or as on the surface of an ordinary rasp file. The textured surface is then distanced from the exposed surface of the base layer such that the elevated points draw out tube-like projections from the exposed surface of the base layer. The base layer and the tube-like projections can be dried to form microneedle arrays. In some cases, the microneedles can be hollow. In other embodiments, the microneedles may be solid. The microneedle arrays can then be cut to form the transdermal drug delivery device.

BRIEF DESCRIPTION OF DRAWINGS

FIG. 5. Shows several fluorescence microscopy images of mouse footpad skin sections demonstrating siGLO Red (fluorescently-labeled siRNA mimic) delivery to the epidermis (or dermis) following administration using a loaded microneedle array. Images A and B show that lateral diffusion dominates the transport of material outward from the delivery site (~90 min timepoint), with comparatively little red fluorescence visible in the dermis (bar=20 μm;). Images C and D show that diffusion was occasionally detected in both the dermis and epidermis (bar=10 μm). Images E and F where taken 30 min after application and show that longer needles are able to deliver to the dermis. All sections were stained with DAPI to visualize nuclei (bar=50 μm).

DETAILED DESCRIPTION OF THE INVENTION

Figure 1A:
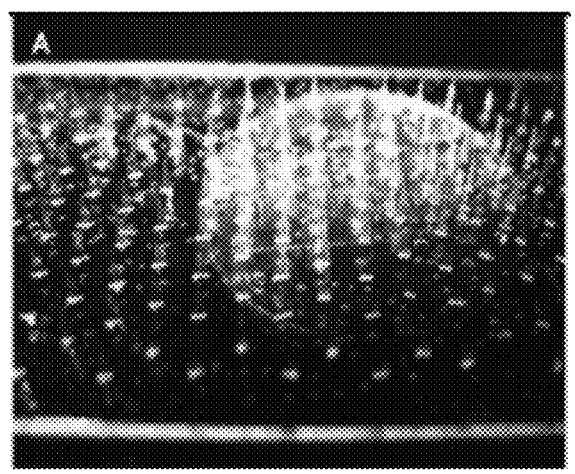
FIG. 1—Shows a microneedle array device showing relative scale. A. The microneedle array shown is supported by a glass substrate, with a penny to show scale. Highly regular arrays of hollow, dissolvable microneedles are formed from a polymer solution film. The array shown has 248 microneedles in an 8 by 31 array, showing 2 or fewer defective needles. B. Shows a close-up of the microneedles of an array clearly showing internal channels in each needle. Solid needles are also possible, by varying fabrication conditions. Bubbles in the base film are similar to those believed to cause the hollows during the needle forming process. The needle tips may be beveled at any angle by trimming. C. C. Shows a needle loaded with fluorescein and under UV illumination. Microneedle array delivery devices may be formed with hollow needles suitable for loading with a variety of materials ("cargo").

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting.

In describing and claiming the present invention, the following terminology will be used.

The singular forms "a," "an," and "the" include plural referents unless the context clearly dictates otherwise. Thus, for example, reference to "a microneedle" includes reference to one or more microneedles, and reference to "the polymer" includes reference to one or more polymers.

As used herein, the term "about" is used to provide flexibility to a numerical range endpoint by providing that a given value may be "a little above" or "a little below" the endpoint.

The term "subject" refers to a mammal that may benefit from the administration using a transdermal device or method of this invention. Examples of subjects include humans, and other animals such as horses, pigs, cattle, dogs, cats, rabbits, and aquatic mammals.

As used herein, the term "active agent" or "drug" are used interchangeably and refer to a pharmacologically active substance or composition.

The term "transdermal" refers to the route of administration that facilitates transfer of a drug into and/or through a skin surface wherein a transdermal composition is administered to the skin surface.

As used herein, the term "substantially" refers to the complete or nearly complete extent or degree of an action, characteristic, property, state, structure, item, or result.

As used herein, sequences, compounds, formulations, delivery mechanisms, or other items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 g" should be interpreted to include not only the explicitly recited values of about 0.5 g to about 10.0 g, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices, and materials are described below.

As discussed above, the present invention provides transdermal deliver devices as well as associated methods of manufacture and use. In one embodiment, a transdermal delivery device is provided. The transdermal delivery device includes a polymer layer which has microneedles projecting from one of its surfaces. The microneedles are compositionally homogenous with the polymer base layer.

The polymer which forms the polymeric layer and the microneedles can be selected from a variety of polymers known in the transdermal drug delivery arts. In one embodiment, the polymer can be bio-absorbable or biodegradable. Non-limiting examples include polyvinyl alcohol (PVA), polyacrylates, polymers of ethylene-vinyl acetates, and other acyl substituted cellulose acetates, polyurethanes, polystyrenes, polyvinyl chloride, polyvinyl fluoride, polyethylene oxide, chlorosulphonate polyolefins, poly(vinyl imidazole), poly(valeric acid), poly butyric acid, poly lactides, polyglycolides, polyanhydrides, polyorthoesters, polysaccharides, gelatin, and the like, mixtures, and copolymers thereof. In one embodiment, the polymer can be an adhesive polymer. In a preferred embodiment, the polymer is polyvinyl alcohol.

Depending on the type of polymer selected, the concentration of the polymer used can be varied in order to obtain the desired microneedle forming properties. In one embodiment, the concentration of the polymeric solution which is used to form the polymeric base layer and the microneedles can have a polymer concentration of from 1 wt % to 50 wt %. In a one embodiment, the polymer can be polyvinyl alcohol and the concentration in the polymeric solution can be 20 wt %.

The microneedles of the microneedle arrays are made from the same material as the polymer base thereby making them compositionally homogenous with the polymer base. The microneedles can be oriented at an angle to the polymer base or they can be configured to be perpendicular to the polymer base. It is preferable that the microneedles are oriented perpendicularly to the polymer base in order to facilitate insertion of the needles into skin surface by pressure normal to the surface. It is also possible to produce and provide a microneedle array which has microneedles with different angular configurations or different needle lengths. In one embodiment, the microneedles can have a length of from about 10 µm to about 10000 µm. In another embodiment, the microneedles can have a length of from about 50 µm to about 1000 µm. In another embodiment, the microneedles can have a length of from about 75 µm to about 500 µm.

Depending on the active agent or drug being delivered as well as the desired length of time of delivery, and the polymer used to form the microneedles, the microneedles can be configured to soften or dissolve such that they detach and are left in embedded in the skin. When the microneedles are configured to be left in a subject even after removal of the polymer base layer, the polymer can be a biodegradable or bio-absorbable polymer. Microneedles which are detached and left embedded in the skin can provide sustained or extended release of the active agent being delivered by the needles. In one embodiment, formed needles can be further loaded by momentarily contacting the needle tips to a second polymer solution, which may contain an active agent. When the needles are withdrawn, a residue of the second polymer solution remains on the tips, or within the tip of the hollow portion of the needles. If this second polymer solution possesses lower water-solubility characteristics that differ from the primary polymer composing the needles, the tip represents a payload that is deposited when the microneedle detaches in the skin, in a manner similar to a harpoon tip. The lower solubility of the payload tip may provide an extended release characteristic if an active agent is incorporated into the tip polymer.

The microneedles can be manufactured to be hollow or solid. When the microneedles are hollow, an active agent or active agent composition can be loaded into the hollow portion of the microneedle which can then be delivered by the needle to a subject. The term "hollow" refers to a region in the interior of the microneedle having a diameter which is sufficient in size to allow the passage of liquid or solid materials into or through the microneedle. The hollow portions of the needle can, but are not required to, extend throughout all or a portion of the needle. In one embodiment, the hollow region can have an opening at the tip of the microneedle. When the microneedles are solid, an active agent or active agent composition can be loaded onto the exterior surface of the microneedle. Hollow needles can be potentially loaded with larger quantities of active agent payload than is possible for solid needles of the same dimension.

The microneedle arrays contained in the transdermal devices of the present invention can be configured to deliver a wide variety of active agents including active agents intended for topical, local, and/or systemic delivery. Generally, any drug or active agent which can be effectively delivered transdermally can be delivered using the microneedle arrays of the present invention. In one embodiment, the active agent can be nucleic acid material, including but not limited to single or double stranded DNA/RNA, plasmids, or the like.

The active agents can be loaded or incorporated into the microneedle arrays in a number of ways. In one embodiment, the active agent can be loaded into the hollow region of the needle. Loading into the hollow regions can be done through capillary action, a pressurized reservoir, or any other means which can be used without damaging the microneedle array. One method of loading the hollow needles can be to bring the needle tips into momentary contact with a solution of an active agent in a volatile material such as water or ethanol. When the tips touch the surface of an appropriate liquid, the liquid can wet into the tips by capillary action, and an aliquot is introduced into only the needle tip, which is believed will produce the most efficient use of the active agent, avoiding waste of material in the non-penetrating portion of the array.

The active agent can also be incorporated into the microneedle through incorporation into the polymer solution from which the microneedle and the polymer base layer are formed. When the active agent is incorporated into the microneedle in this manner the active agent is also incorporated into the polymer base layer. When the active agent is incorporated directly into the polymer of the microneedle, the microneedles deliver the drug in a similar manner as the matrix layer in traditional transdermal matrix patches. However, the microneedles may provide the additional benefit of providing local disruption of skin barrier structures, facilitating the entry of drugs which might not normally penetrate skin in a transdermal matrix patch delivery system.

In another embodiment, the active agent(s) can be incorporated into the microneedle by first loading an active agent solution onto the protrusions of the textured surface or template used to draw out the needles from the base layer. In this case, the active agent(s) are typically observed to be localized in the needle structure, with little or no migration into the base layer. A variety of other methods of loading the needles may be apparent to one of ordinary skill in the art to which this invention belongs, and these methods may include contact with solutions, or vapor or powder forms of active agent compositions. Choice of methods by which needles are loaded may be dictated by the particular active agents and details of the desired application for that particular microneedle array product.

The microneedle arrays can be incorporated into a variety of transdermal delivery devices such as transdermal patches 108. In one aspect of the invention, the polymer base layer 104 of the microneedle array can be attached to a backing layer 106 to form a transdermal patch. In another aspect, the polymer base layer can be associated with or attached to an active agent reservoir from which active agent can be delivered through the microneedles to a subject. The reservoir layer can be a liquid reservoir or a hydrogel reservoir or any other reservoir type known in the arts so long as the reservoir can adequately deliver the active agent to the microneedles. Other material may also be incorporated into the transdermal delivery devices of the present invention such as permeation enhancers, controlled-release membranes, humectants, emollients, and the like.

The microneedle arrays can be used as or incorporated into transdermal delivery devices to administer active agents transdermally. The microneedle arrays of the transdermal delivery devices can be applied to a skin surface of a subject in order to deliver the active agent to the subject. The administration can be for a sustained or an extended period of time. Sustained delivery of the active agent can be accomplished by using microneedle arrays in which the microneedles can be detached and remain in the skin of the subject even after removal of the rest of the transdermal delivery device, including the polymer base layer. Microneedles left in the skin of a subject act as active agent reservoirs and can delivery active agent even after the transdermal delivery device is removed.

The microneedle arrays used in the transdermal delivery devices of the present invention can be made in any manner known in the art so long as they comply with the other requirements set forth above. One method of manufacturing or forming the microneedle arrays is provided herein. The method involves providing a substrate and then applying a polymer solution to the substrate to form a base layer. An exposed surface of the base layer is then disposed with a textured surface having elevated points protruding there from such that the elevated points contact the exposed surface of the base layer. The textured surface is then distanced from the exposed surface of the base layer such that the elevated points draw out hollow tube-like projections from the exposed surface of the base layer. The textured surface can be made of any material known in the field and can be configured in any manner which allows it to contact the base layer and draw out the microneedle protrusions as described herein. Once drawn out, the microneedle protrusions can be sharpened or otherwise shaped using any method known in the art.

The base layer and the hollow tube-like projections can be dried to form microneedle arrays. The microneedle arrays can then be cut to form the transdermal drug delivery device. Methods for cutting or forming the transdermal drug delivery device are well known in the art, including but not limited to die cutting or other physical shearing, thermal melting, thermal degradation, laser ablation, chemical degradation, dissolution, freeze fracture, sonication of the template, or any other physical or chemical known in the art. It is important to note that the manufacture of the needles can be done in single batch or continuous batch methods. When a continuous manufacturing method is used, any mechanized means known in the art can be used. For example, the surface used to draw out the microneedle protrusions could be a roller having numerous rows of protrusions which are configured to contact and draw out the microneedles from the base layer. Other mechanized and automated manufacturing techniques and technologies used in the manufacturing arts can be retrofitted and used in the production of the microneedles of the present invention.

The substrates used in the manufacture of the microneedle arrays can be any solid or porous material onto which a polymer solution can be applied. Non-limiting examples of substrate layers include glass, backing layer materials including woven and non-woven material, etc.

As discussed above, a variety of polymers and polymer solution concentrations can be used in order to form the microneedles of the present invention. The polymer solution can be applied to the substrate in order to form a polymer base layer. The polymer base layer generally has a thickness from about 0.5 mm to about 5 mm. In one embodiment, the polymer base layer can have a thickness of from 0.5 mm to about 2 mm. In on embodiment, the polymer base layer has a thickness of about 1 mm.

Figure 1B:
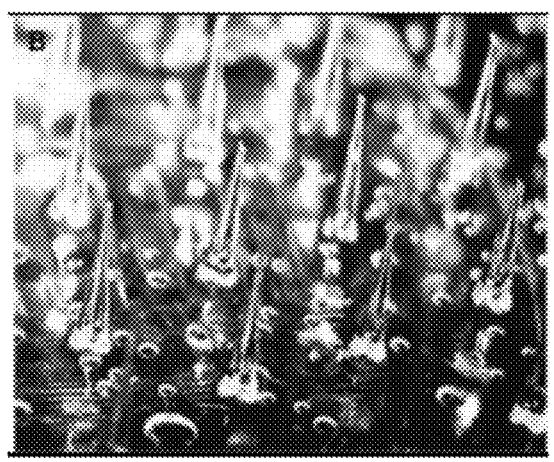
Figure 1C:
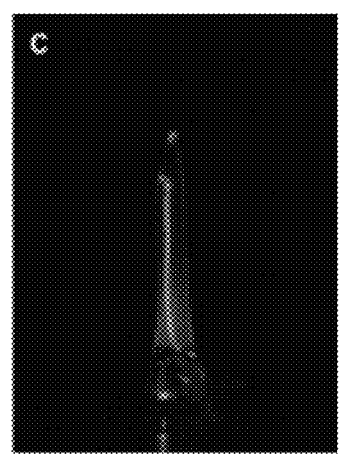

The textured surface which contacts the exposed surface of the polymer base layer has raised regions or points which contact the polymer base layer. The raised regions can be regularly spaced on the textured surface in order to form regularly spaced microneedles. The number of raised regions on the textured surface and correspondingly the number of microneedles formed can be a factor of the active agent or drug being delivered as well as the amount or dosage of the active agent. Such a determination could be made by one of ordinary skill in the art. FIG. 1 shows an array of microneedles formed using the method described herein from a 30 wt % polyvinyl alcohol solution.

Figure 2:
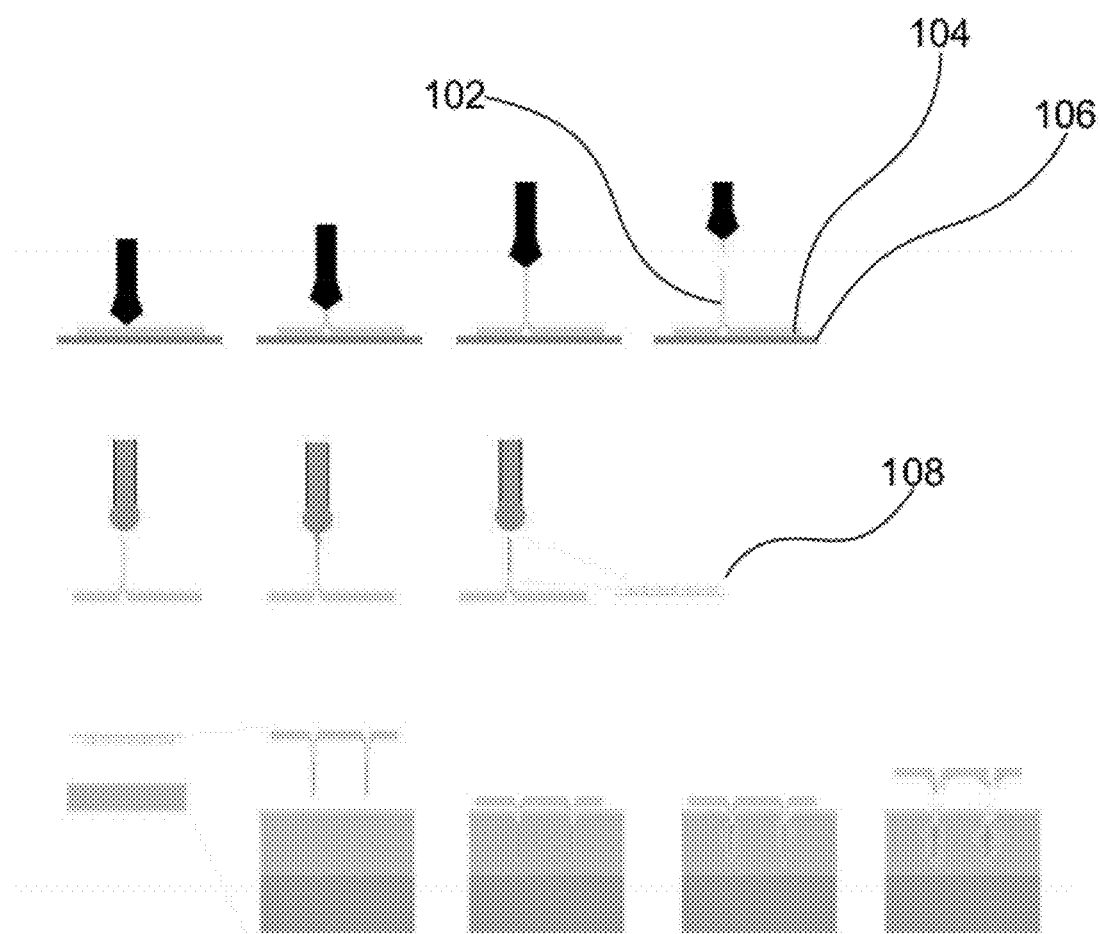
FIG. 2—Shows a schematic of a microneedle array preparation. Needles are prepared from a polymer (e.g. polyvinyl alcohol (PVA)) film by "drawing out," leaving a hollow tube. The ends are clipped to give desired shape of needle end (and length). The resulting hollow tubes are "charged" with an active ingredient, such as nucleic acids (e.g. plasmid or siRNA). The cured (hardened) microneedle array is inserted into the skin. In the aqueous environment of the epidermis, the needles soften and deform, and the inserted portion will separate (leaving the "charged" tips in the epidermis) as the backing material is removed after an initial application period. As the PVA solution dissolves, the cargo is slowly released into the target epidermis.
Figure 3A:
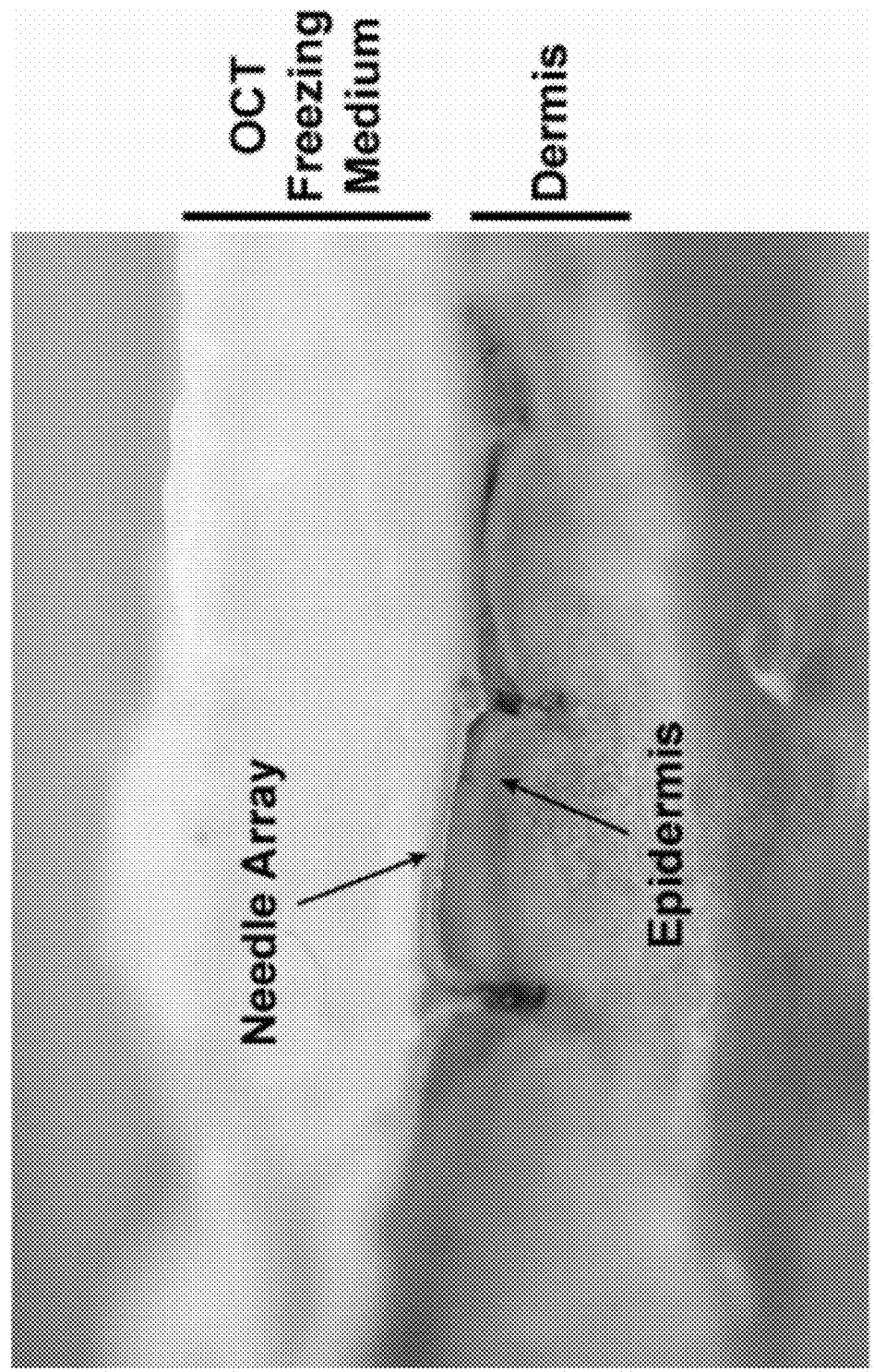
FIG. 3—Shows a cross-section of excised human skin showing penetration by needles loaded with gentian violet. A. The microneedle delivery device was loaded with gentian violet solution as a visual reporter ("cargo") and was applied to fresh human skin explant (resulting from an abdominoplasty procedure) and then immediately placed into tissue freezing medium (OCT) and cooled to −28° C. The sample was sectioned at an angle nearly parallel to the needle array geometry, allowing observation of multiple needles. The delivery device backing material is visible as a layer between the OCT and the skin sample. The left needle is itself cross-sectioned, showing the gentian violet solution loaded into the needle shaft. The middle needle appears to penetrate both the stratum corneum and the epidermis, with the needle tip in full contact with the dermis. A third needle (on the right) is visible but is out of the focal plane. B. Shows the gentian violet delivered to human epidermis and dermis using the microneedles. The Gentian violet was detected using a fluorescent microscope under red fluorescence filters (excitation 546 nm; emission 580 nm). The skin section was stained with DAPI to allow nuclei visualization.
Figure 3B:
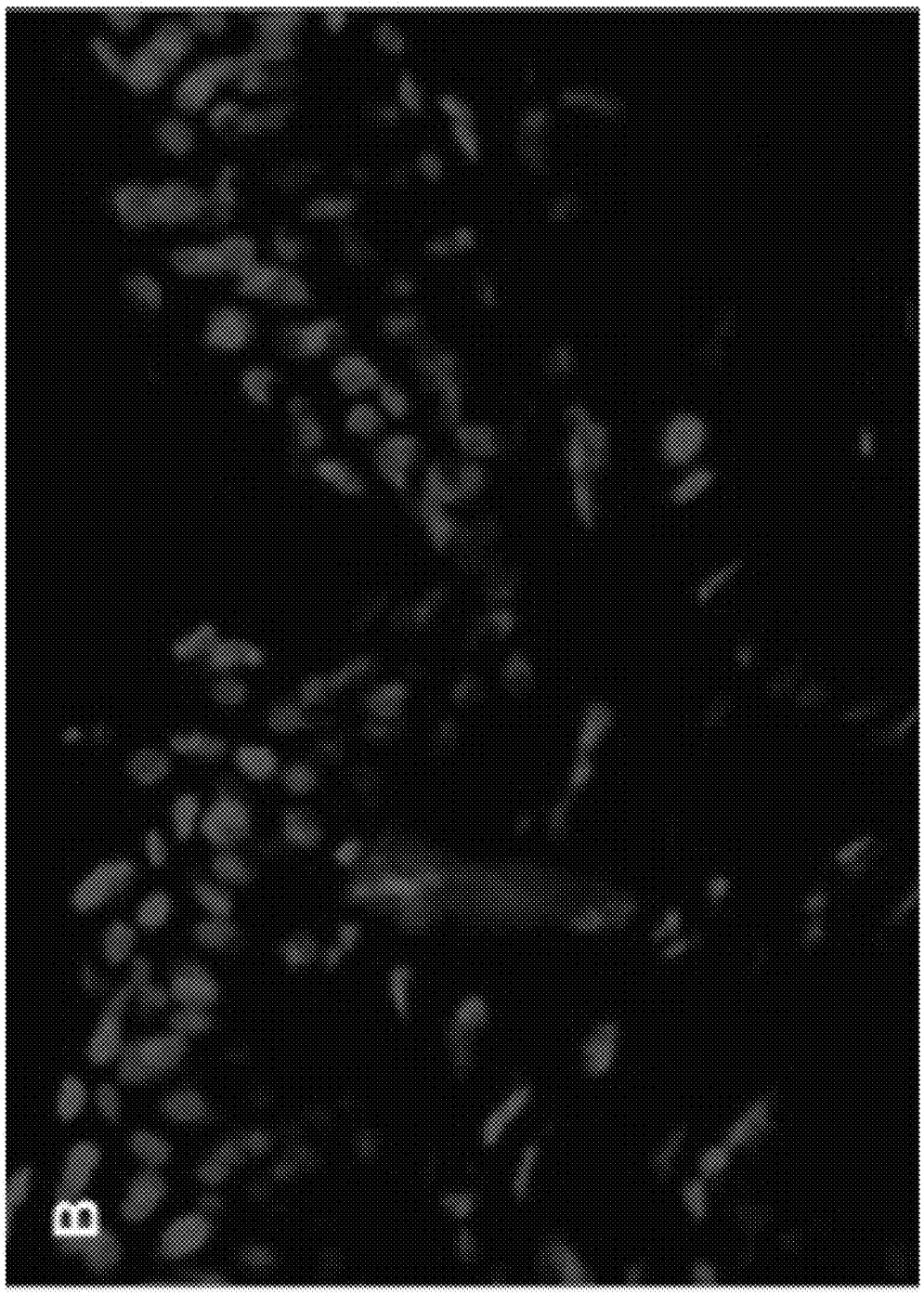

The length of the microneedles formed is a function of the distance that the textured surface is distanced or drawn away from the polymer base layer. As discussed above, the microneedles can have a length of from about 10 µm to about 10000 µm. FIG. 2 shows a schematic of the drawing process which can be used to form the microneedle arrays. After the microneedles 102 are drawn or formed, the polymer base layer 104 and the microneedles of the array can be dried by baking, blowing, other drying means, or combinations thereof. In one embodiment, drying of the microneedles and the polymer base layer can occur during the distancing step in which the microneedles are formed. It is noted that when loading of the microneedles occurs after the initial drying it can be desirable to perform an additional drying or baking step subsequent to the loading of the needles with an active agent composition. Baking the needles at about 80° C. for about 1 hour increases their rigidity, forming microneedles sufficiently rigid to penetrate through the stratum corneum and into deeper skin layers (FIG. 3). Use of increased air flow rates, or reduced pressure as in a vacuum oven may decrease the temperature and curing time required.

While not wishing to be bound by any particular theory, generally, the increased needle rigidity required for skin penetration is understood to be a function of solvent evaporation rather than a chemical transformation, and any process by which solvent may be removed is understood to accelerate needle hardening. Further, it is believed that the shape and structure of the needles is highly dependent on the dynamics of the drying process. The length of the needles is directly dependent upon the distance to which the template is retracted from the surface of the polymer film base layer from which the needles are pulled. However, the rate at which the template is retracted and rate at which the film dries act together to determine the morphology of the needles formed. If the template is withdrawn too quickly relative to the drying rate, the strand of polymer solution connecting each template protrusion may be stretched beyond its capacity to flow and deform, and the strand may fail, prematurely separating the template protrusion from the film. If the drying rate is too fast relative to the rate of retraction, the entire film surface may dry to form an elastic film rather than an inelastically deformable or flowable gel. If the film dries sufficiently to behave as an elastic solid before the template protrusion is completely withdrawn, the film may tear or separate from the substrate, producing an unacceptably deformed or non-uniform needle array. However, between these two extremes, lies a range of acceptable drying rates relative to any particular rate of retraction of the template protrusions from the base polymer solution film. In one embodiment the template can be retracted from the base at a rate of 0.1 mm/s to 100 mm/s with a heated airflow drying the of 0.1 to 10 m/s at a temperature of 0° C. to 100° C. In another embodiment, the template can be retracted from the base at a rate of 1 mm to 50 mm/s with a heated airflow drying the of 0.5 m/s to 7 m/s at a temperature of 20° C. to 70° C. In yet another embodiment, the template can be retracted from the base at a rate of 2 mm/s to 15 mm/s with a heated airflow drying the of 0.75 m/s to 5 m/s at a temperature of 25° C. to 50° C.

When the drying rate of the polymer film is well matched to the rate of template retraction in the present invention, the base polymer film remains fluid and inelastically deformable, while the strands formed between the template protrusions and the base film dry more quickly than the base layer, and rapidly become inelastic, which permits longer fiber-like needle structures to be drawn out of the still wet film. In effect, the drier elastic portion of the strand plays the role of the template projections relative to the wetter inelastically deformable base layer. Without being limited by any particular theory, it is believed that the strands dry more quickly than the base layer primarily due to a large ratio of drying surface area versus internal volume, as compared to the base layer which has a lower drying surface area versus its internal volume. Additionally, air flow patterns further away from the film surface may very likely contribute to this effect, particularly if drying is promoted by flowing air over the needles as they are formed.

Any method may be used to promote or control the drying process, including methods that use air flow, heat or cooling, pressurization or vacuum, humidity, or any other method familiar to those skilled in the art of polymer processing. Further, to the extent that the polymer solution rheology or elasticity may be influenced by factors other than simple drying, such as temperature, chemistry, photochemical effects, sonic or vibrational energy, or other methods known to those skilled in the art of polymer processing, these methods may also reasonably be applied to accomplish the same effects in the needle drawing process.

As the needles are drawn out from the base polymer layer as described above, it is understood that as the surface of the base film dries to form an elastic layer, this layer becomes more and more pulled onto the strands being drawn from the film. If the air flow is such that the surface of the base layer dries to relative inelasticity in the last one or two millimeters of the template withdrawal, it is deformed more substantially in these last millimeters of withdrawal, to form a wider base. Surprisingly, it is observed that the formation of this wider base is accompanied by the formation of a hollow space within the needle. Without being limited by any particular theory, it is believed that the tension produced by the withdrawal of the protrusions from the film during its transition to elastic behavior creates a region of lower pressure between the drying surface and the wetter solution beneath the film surface, and that this lower pressure induces evaporation of some of the water of the solution to form a pocket rich in water vapor. Independent of the actual cause or contents of the void area, a hollow needle is the result.

Another aspect of the incorporation of the drying surface into the needle base is that if an active agent is distributed only upon the surface of the polymer solution layer. For example, by applying a small quantity of a solution of the active agent within a more volatile material such as ethanol, it is observed that a disproportionate quantity of the active agent is incorporated into the base of the needles. This is readily observed by use of a colored active agent such as fluorescein.

EXAMPLES

Example 1

Production of Microneedle Array

Microneedle arrays were prepared according to the following steps:
1. A 0.3 gram aliquot of approximately 30% polyvinyl alcohol [PVA] (Spectrum Chemicals, Gardena, Calif.) solution in water was spread in a uniform thin layer to cover approximately the entire surface of a standard glass microscope slide (roughly 25 by 75 mm).
2. A common rasp-type file was placed with the working surface facing up on the laboratory bench, and the slide was lowered PVA-side down, so that the PVA layer was brought into contact with the file working surface. The slide was then gently pressed down so as to wet the tips of the file points with the PVA solution.
3. A common hair dryer set to low was used to direct a stream of approximately 60° C. air flowing at approximately 4 m/s over the file and slide thus assembled from a distance of about 1 foot, blowing horizontally along the laboratory bench surface, with the intent to dry and heat the needles as they were formed.
4. Immediately after directing the warm air stream over the work piece, the slide was carefully removed from the file by lifting it straight up from the file surface to a height of approximately 15 mm above the file points. The file was held in place, so that it was not pulled up by adhesion to the slide. From each file point, a hollow tube was drawn up from the film surface, the hollow being formed from a bubble at the needle base, apparently created or enhanced by the pulling action.
5. The slide was kept positioned exactly over the file to avoid flexion or distortion of the newly formed needle structures, and the warm air stream was continued for about 10 minutes to dry the needles and the PVA film from which they had been formed.
6. The air stream was stopped, and the needles were cut off of the file surface by running a standard single-edged razor blade parallel to the file surface, just above the file rasp tips. The needles were smoothly and easily sliced just above their point of contact with the file rasp tips. The rasp tips were spaced such that a regular array of needles was formed in the film in 8 columns of 31 rows each, forming 248 needles, of which 2 were either bent or deformed such that they appeared not useful as needles, and the remaining 246 needles appeared capable.
7. The PVA film was removed from the glass substrate by sliding a standard single-edged razor blade between the edge of the film and the glass, which permitted a smooth separation, something between peeling and slicing the film away from the glass.
8. The needles were trimmed to a height of about 3 mm using a pair of typical cuticle-type scissors purchased from the local Longs Drugstore. Trimming was performed under an inspection microscope to facilitate visualization of the small structures, and the needle tips were cut at approximately 45 degrees to normal, to form a sharp, beveled tip.
9. Needles were loaded with pcDNA3.1 fLuc expression plasmid (10 mg/ml) at approximately 200 ng/needle in phosphate buffer solution (PBS) and then baked at 90° C. in a typical consumer toaster oven with the door open for about 60 minutes, then cooled for 10 minutes. This baking step was performed to dry and harden the needles to sufficient rigidity for skin penetration. A similar control needle array was prepared using the carrier (PBS) alone.
10. The needle arrays (fLuc expression plasmid or PBS control) were pressed into the ears of an anesthetized (isoflurane) mouse using finger pressure for approximately 20 minutes at which time the needle arrays were removed. The mice were allowed to sleep for an additional 25 minutes.
11. After 24 hours, the mouse was administered 100 µl of 30 mg/ml luciferin by intraperitaneal injection. Following a 10 minute incubation to allow biodistribution of the luciferin, the mice were anesthetized with isoflurane and imaged for 5 minutes (light emission captured) using a Xenogen IVIS200 imaging system, which showed unambiguous signal localized at the site of microneedle administration, demonstrating expression of the injected plasmid.

Example 2

Manufacture of a Loaded Microneedle Array

Microneedle arrays of the present invention were prepared as set forth below:
1) A solution of polyvinyl alcohol (PVA) (Spectrum Chemical, Gardena, Calif.) is prepared by dissolving 19 grams of dry PVA in 81 grams of distilled water (DI) at 80 C for 24 hours, stirring the thick solution manually every 3 hours after the first 12 hours. The solution is transferred hot to suitable containers for subsequent dispensing (such as two 50 mL plastic syringes) and cooled to room temperature prior to use.

2) A solution of Carboxymethylcellulose Sodium solution (CMC) (Spectrum Chemical, Gardena, Calif.) is prepared by dissolving 2 grams CMC in 98 grams of DI at 80 C for 24 hours, stirring continuously on a hotplate/magnetic stirrer. The solution is transferred to a glass jar with a screw cap and cooled to room temperature before use.

3) An ordinary microscope slide measuring 25 by 75 mm by 1 mm thick is coated with roughly 0.5 grams of the 2% CMC solution described above by the following method. The microscope slide held by forceps at one short (25 mm) edge, and dipped into the CMC solution until roughly 55 mm are below the surface, with 20 mm remaining unwetted by the CMC. The slide is withdrawn from the CMC solution and one side is scraped off using a spatula or other straight edge. The scraped side is then wiped against a laboratory wipe or other absorbent material to dry and remove the majority of CMC solution, leaving a roughly cleaned bottom face, with a top face coated in the CMC solution. The slide is placed on a level surface in an air stream of 3 m/s at 50° C. until visibly dry, roughly 15 minutes. The CMC solution is sufficiently fluid to flow across the surface, producing a roughly uniform coating on the slide. The dried layer produced by this method serves as a release layer for the subsequent PVA coating to be applied for needle formation. The final dried weight of the CMC film is approximately 0.01 g, and the film thickness is apparently thinner than 0.1 mm as gauged by eye.

4) A microscope slide that has been pre-treated with CMC as described above is coated with PVA preparatory to forming needles by the following procedure. A roughly 0.75 gram aliquot of an 19% PVA solution is deposited on one end of a CMC pre-treated microscope slide, and spread to a thickness of 0.5 mm using a spatula or similar straight edge. A sufficiently uniform 0.5 mm layer thickness is produced by the use of two 1.5 mm rails on either side of the slide. The underlying dry CMC layer thickness is apparently negligible compared to the thickness of the subsequent PVA layer, and is not considered in the application thickness of the PVA layer. The layer produced is roughly 40 by 25 mm wide, and 0.5 mm thick.

5) The microscope slide coated with PVA solution described above is mounted in a chuck or clamped to prevent it from moving. By means of a motion control device such as a pneumatic actuator, a template of rigid pins is brought into contact with the PVA solution to a depth of at least 0.2 mm. Heated air is flowed across the substrate and pins at approximately 35° C. and 1.0 m/s and the pins are permitted to remain in the drying film for about 5 seconds and then retracted 1 cm at a rate of about 5 mm/s. About halfway through the retraction, after 10 seconds, an additional airflow is introduced at 50° C. and 2.0 m/s. The initial effect of retracting the pins is to produce stringlike fibers from the PVA solution. As the PVA solution is pulled from the base layer by the pins, the airflow dries the thin fibers much more rapidly than the base layer. However, when the airflow is increased halfway through, the fibers dry much more rapidly, and the drying region is understood to be much closer to the base layer, and a thicker fiber results. Surprisingly, under the conditions described above, this thicker fiber develops a void, likely due to heated water vapor, and subsequent retraction of the pins results in formation of a hollow tube rather than a sealed fiber. If the stronger heated airflow is initiated too early, the base film dries too quickly and sheets of PVA film are pulled away rather than discrete fibers, even to the point of separating from the glass slide. If the stronger heated airflow is not initiated, hollow fiber formation does not occur reliably, and the solid form is the typical outcome. The form of the needles is strongly influenced by the uniformity, temperature, and rate of air flow, and these must be optimized to produce reproducible desired results. The values provided here are exemplar, and any particular apparatus may require slight adjustments to these parameters.

6) The stronger heated airflow is maintained for approximately 15 minutes until the base PVA layer has dried to a thickness of approximately 0.1 mm, and is an elastic solid rather than a liquid. The array is preferably further dried at 25° C. for 24 hours at approximately 30-50% humidity, and then separated from the glass substrate by use of a razor blade or similar sharp implement. The CMC layer permits easy removal by this method, and prevents the PVA from bonding more permanently to the glass.

7) The array of needles prepared as described above is separated from the template pin array by slicing the needles with a razor blade. It is convenient to slice the needles close to the template pins to leave minimal PVA residue on the pin array, which may be rapidly cleaned by immersion in water at 80° C. The needles are then manually trimmed with miniature shear-type scissors, such as manicure scissors, to produce needles of a desired length and tip-bevel. After an initial 24 hour 25° C. drying time, needles and backing material are easily cut, and very flexible, although resilient. It is easier to cut the needles before further drying, but not required.

Steps 8-10 may be included in the original manufacture or can be performed at a later time.

8) Needles may be loaded by bringing the needle tips into contact with a solution of the desired payload, or any liquid form of the payload. Lower viscosity (such as ethanolic) 1-100 cSt solutions are most easily loaded, but higher viscosity up to around 1000 cSt aqueous solutions of macromolecules may also be loaded by this method. A preferred method of loading individual needles is to use a plastic dispensing pipette tip or similar, which permits entry of the needle into the tip, but inhibits the tendency of solution surface tension to wet across the PVA base layer, and impedes evaporation of the payload solution from the dispenser. Multiple needles can be loaded simultaneously by use of multiple tips spaced at intervals aligned with needle spacing.

9) After loading, the PVA matrix forming the needle structures frequently becomes hydrated and softens. In order to prepare the needles for use in injecting the payload material, further drying is required. This drying may be accomplished by simple heating in an airflow, but to prevent degradation of sensitive biological molecules it is useful to use a vacuum oven. Typically 12 hours drying at −20 lbs vacuum and 50° C. produces highly rigid needles that are useful for injection.

10) If the payload in the needles was introduced in aqueous solution, the sharp tips of the cut needles may be solubilized in the loading process, and the final dried form may show rounding of the initially sharp tip. In such case, it is useful to re-trim the needle tips to produce a freshly cut sharp edge following the final drying step.

Example 3

Loading Hollow Microneedles with an Active Agent

Hollow microneedles, such as those formed by the method of Examples 1 or 2 can be loaded with an active agent. A method of loading such hollow needles is to bring the needle tips into momentary contact with a solution of an active agent in a volatile material such as water or ethanol. When the tips touch the surface of an appropriate liquid, the liquid can wet into the tips by capillary action, and an aliquot is introduced into only the needle tip, which is believed will produce the most efficient use of the active agent, avoiding waste of material in the non-penetrating portion of the array. After loading, the needles can be baked at about 100° C. for about 1 hour to increase their rigidity, and they have been found to be sufficiently rigid to penetrate through the stratum corneum and into deeper skin layers.

When the needles are significantly hydrated, they frequently soften to a flexible, rubbery state, retaining their basic shape and orientation, but no longer sufficiently rigid to penetrate skin. Longer exposure to solvent can potentially deform or dissolve the needles, but the short exposure to the low volumes used for loading does not typically produce that result. If the needles are rubbery after loading, a second dehydration process is required to produce sufficient rigidity and hardness for skin penetration. Generally this takes place through baking at around 100° C. for 1 hour, but it is expected that desiccation by a drying agent, reduced pressure, or any other process would achieve a similar effect.

Example 4

Identification of Polymers for Use in Preparing Microneedles

Aqueous solution concentrations (10-50% weight/volume or maximum flowable at 25° C.) of various USP polymer materials acceptable for parenteral use for fiber-extrusion/draw characteristics using a standardized air flow of 5 cfm at 50° C. were prepared. Suitability for fiber draw can be determined by capability of the polymer solution to form a stable, reproducible nascent fiber structure of at least 1 cm (various polymers are expected to require different working speeds under arbitrary conditions, but a suitable candidate material should exhibit this minimum capability). Polymers to be tested include, but not limited to, the following: alginic acid, carboxymethylcellulose, hydroxypropylmethylcellulose, gelatin, guar gum, gum acacia, polyacrylic acid, polyvinyl alcohol, and polyvinylpyrrolidone, all available from Spectrum Chemical (Gardena, Calif.).

Example 5

Identification of Possible Solution Concentrations

The solutions of Example 3 were tested to determine which of the solution has the best dry film qualities. Amounts of each of the solutions can be formed on glass substrates to form films having 1 mm film thickness over a 25 mm by 75 mm area. The films are then dried by baking at 90° C. for 1 hour and inspected for bubble formation, which is an indicator of the relative water permeability of the drying film surface. The films are then cooled, and the cooled films are then qualitatively ranked regarding the following characteristics: difficulty of removal from glass substrate, ductility, brittleness and stiffness. Any materials that produce films that are insufficiently rigid to span a 5 cm gap unsupported can be deemed unsuitable. The films are also qualitatively ranked by resistance to shear and slice cutting by standard scissors and by razor blade, providing an indication of working resistance and film toughness.

Example 6

Testing of the Dissolution of the Films

Films identified in Example 4 are tested and quantitatively ranked with regard to their dissolution rate. Materials that produce films that completely dissolve within 10 seconds are generally not as desirable. Time to non-rigidity and time to flowability are recorded as a possible basis for predicting needle solution dynamics expected after injection.

Example 7

Testing Polymer Solutions for Needle Formation

Films of each solution are prepared as in Example 4, and template protrusions (8 columns by 31 rows of points) are contacted and withdrawn in a standard airflow of 50 cfm at 50° C., using a draw speed appropriate to each material as identified in Example 3. Resulting arrays will be evaluated with respect to needle dimensions and morphology, with preference given to straight, tapered, hollow needles with tip cross-sectional area being approximately 10% of the base cross-sectional area. Candidate material is selected, based on quality of needle array, further qualified by dissolution and rigidity characteristics relative to other materials and by subjective evaluation of ease-of-workability.

Example 8

Identification of Optimal Needle Formation Conditions

Test solutions of 20%, 30%, 40%, and 50% (or maximum flowable at 25° C.) concentration are prepared for use in needle drawing as in Example 6 under several airflow conditions including 1) 50 cfm at 50° C. 2) 100 cfm at 50°, and 3) 50 cfm at 80° C. The relative draw speed required for optimal needle formation under each airflow condition, 5 replicates, is observed and recorded. This data identifies a rough process concentration, temperature, and airflow window. Conditions capable of good needle characteristics with maximum draw speed will be selected as optimal.

Example 9

Identification of Optimal Pre-Bake Drying Conditions

Needle arrays as prepared and tested in Example 7 are tested to identify optimal pre-bake drying times. After drawing, the arrays are dried in place under airflow identical to the draw process for various times. Arrays are then be dried at 5, 10, 20 or 40 minutes under this airflow and separated from glass substrates. Optimal drying conditions will be identified on the basis of best substrate removal characteristics.

Example 10

Identification of Optimal Curing Conditions for Loaded Microneedles

Microneedle arrays as described in Example 8 are manually trimmed to 3 mm length, with 2 sets of the 8 columns each trimmed at nominal tip bevels of 0 (flat), 30, 45, and 60 degrees. Needles are then loaded with 5 µL ethanolic solution of 2% Gentian Violet (Spectrum Chemicals) and 5% fluorescein (Spectrum Chemicals) (approximately 50 nL per needle). Groups of 5 arrays are pre-weighed, baked at temperature of either 60° C. or 80° C., for 30, 40, 50, 60, or 70 minutes and weighed then again. Needles are then qualitatively evaluated for rigidity for each set, with optimal conditions identified as those producing maximum rigidity with the shortest cure time. Any melting or discoloration of arrays will cause this bake condition to be rejected. Rigidity is expected to correlate with moisture loss, indirectly measured by change in mass. Any needle arrays observed to be insufficiently rigid are re-cured at the same temperature in 10 minute increments until minimum required rigidity is attained. Curing temperature and duration are compared in the presence or absence of a vacuum.

Example 11

Testing of Needle Penetration and Active Agent Delivery

Needle array assemblies as described in Example 9 are applied to human skin explants (resulting from abdominoplasties of de-identified patients with informed consent) and left in the skin for 1-60 min. Explants (with or without the needle array) are then frozen in OCT and sectioned using a Leica Jung Frigocut 2800E cryotome. Sections are then mounted on microscope slides using Histomount (Sigma) with DAPI stain for visualization of nuclei. Sections are analyzed for needle penetration and depostition of fluorescein and gentian violet by brightfield and fluorescence microscopy (Zeiss AXIO Observer A.1).

Example 12

Delivery of Fluorescently-Labeled siRNA Using Microneedles

Microneedle arrays are loaded with 10 mg/mL siGLO Red siRNA (Dharmacon #D001830-02) or Cy3-labeled K6a siRNA in water as described for fluorescent dyes in Example 9. The loaded microneedle arrays are applied to human skin and left in the skin for 1-60 min. Treated explants are frozen in OCT and sectioned (7-10 micron) using a Leica Jung Frigocut 2800E cryotome. Sections are mounted on microscope slides using Histomount (Sigma) with DAPI stain for visualization of nuclei. Sections are analyzed for Cy3 expression using Zeiss Axio Observer.A1 fluorescence microscope equipped with the DAPI and DsRed filters.

Example 13

Penetration of Microneedles into Human Skin

A microneedle array in the transdermal delivery device loaded with gentian violet solution was applied to fresh human skin explant (resulting from abdominoplasty procedure) and immediately placed into tissue freezing medium (OCT) and frozen to −28° C. The sample was sectioned at an angle nearly parallel to the needle array geometry, and multiple needles were observed (FIG. 3). In FIG. 3, the microneedle array transdermal delivery device backing material is visible as a layer between the OCT and the skin sample. The left needle is itself cross-sectioned, showing how the violet solution was drawn into the needle shaft by capillary action. The needle at picture center of FIG. 3 appears to penetrate both the stratum corneum and the epidermis, with the needle tip in full contact with the dermis. A third needle is visible at right (out of the cut plane) and is apparently penetrating to a similar depth.

Example 14

Administration of fLuc to a Mouse Ear Using Microneedle Arrays

Figure 4A:
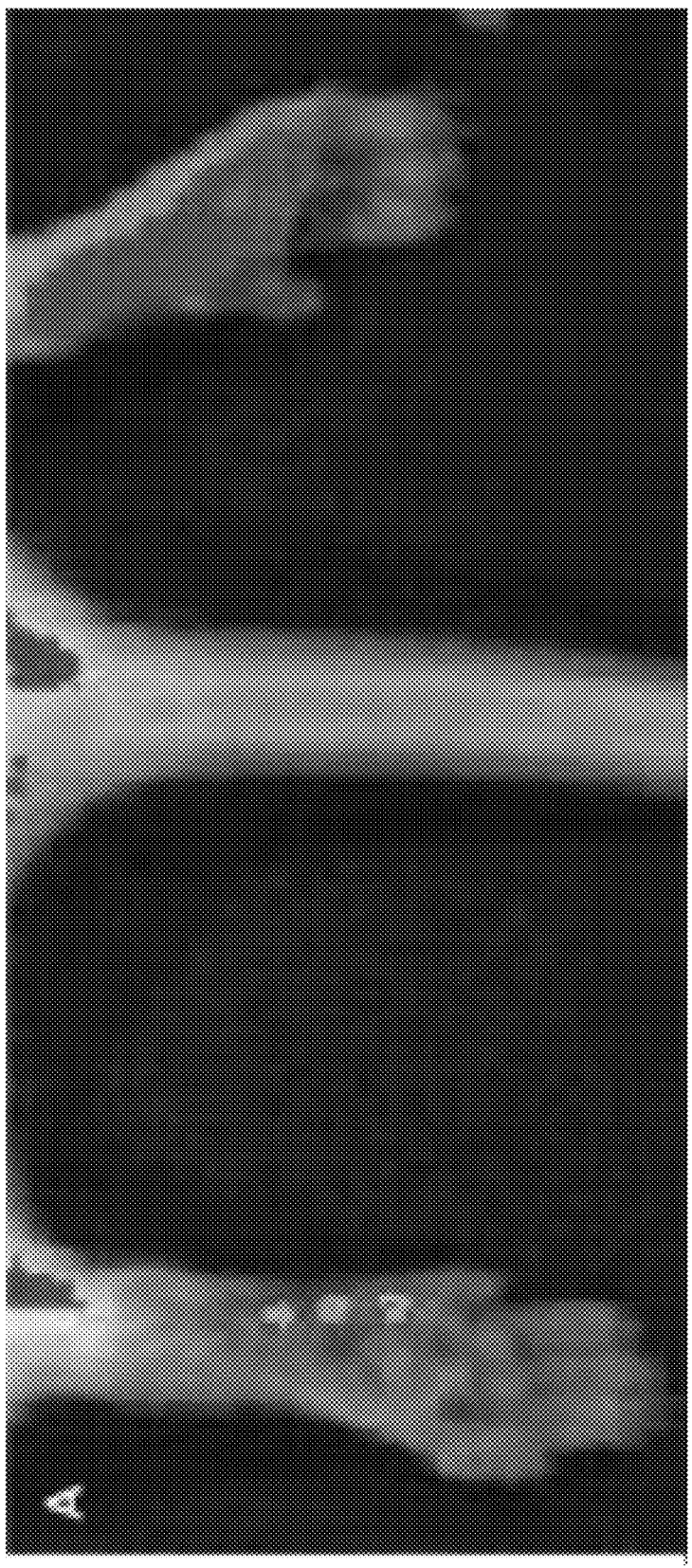
FIG. 4—Shows in vivo imaging of individual microneedle penetration sites and visualization in skin sections. A. Shows localized fluorescence observed using the Xenogen IVIS 200 system to view the left mouse footpad of a mouse to which had been applied a microneedle array loaded with siGLO Red (a fluorescently-tagged siRNA mimic, 0.05 μg per needle) B. Shows fluorescence microscopy of mouse footpad longitudinal skin sections. C. Shows fluorescence microscopy of mouse footpad cross sections of needles loaded with siGLO Red demonstrating delivery to the epidermis. All sections were stained with DAPI to visualize nuclei (bar=10 μm).
Figure 4B:
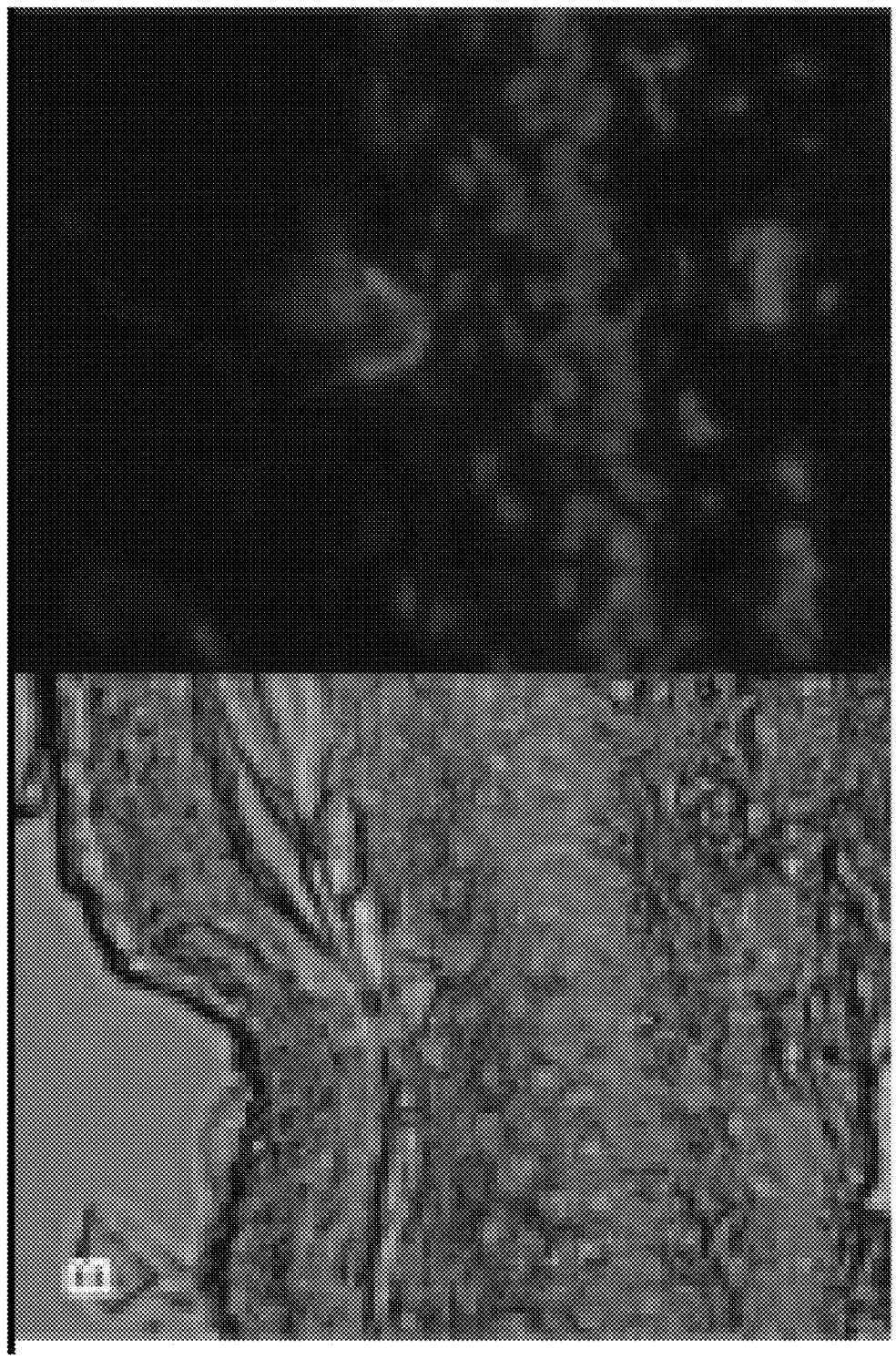
Figure 4C:
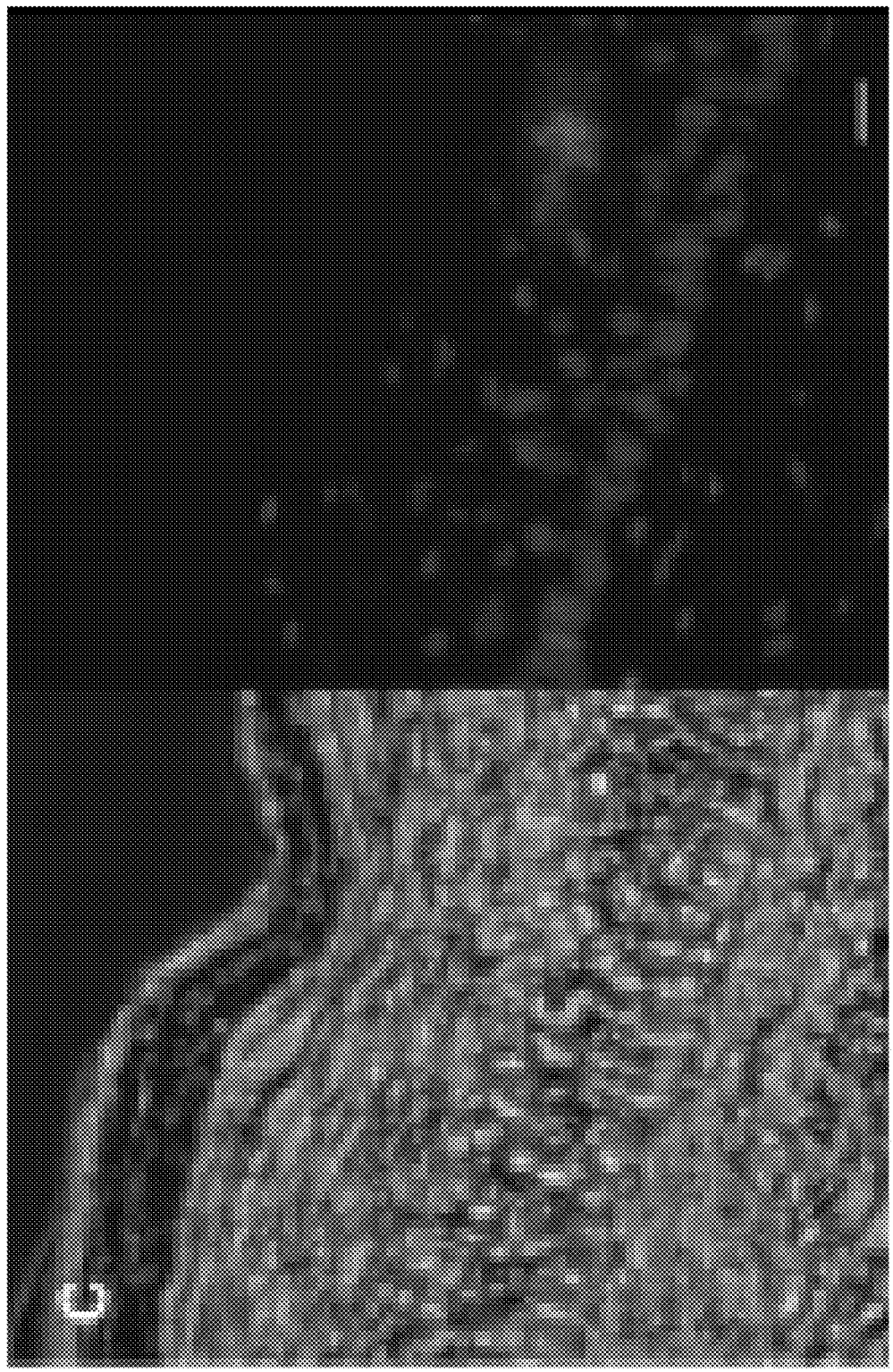
Figure 6A:
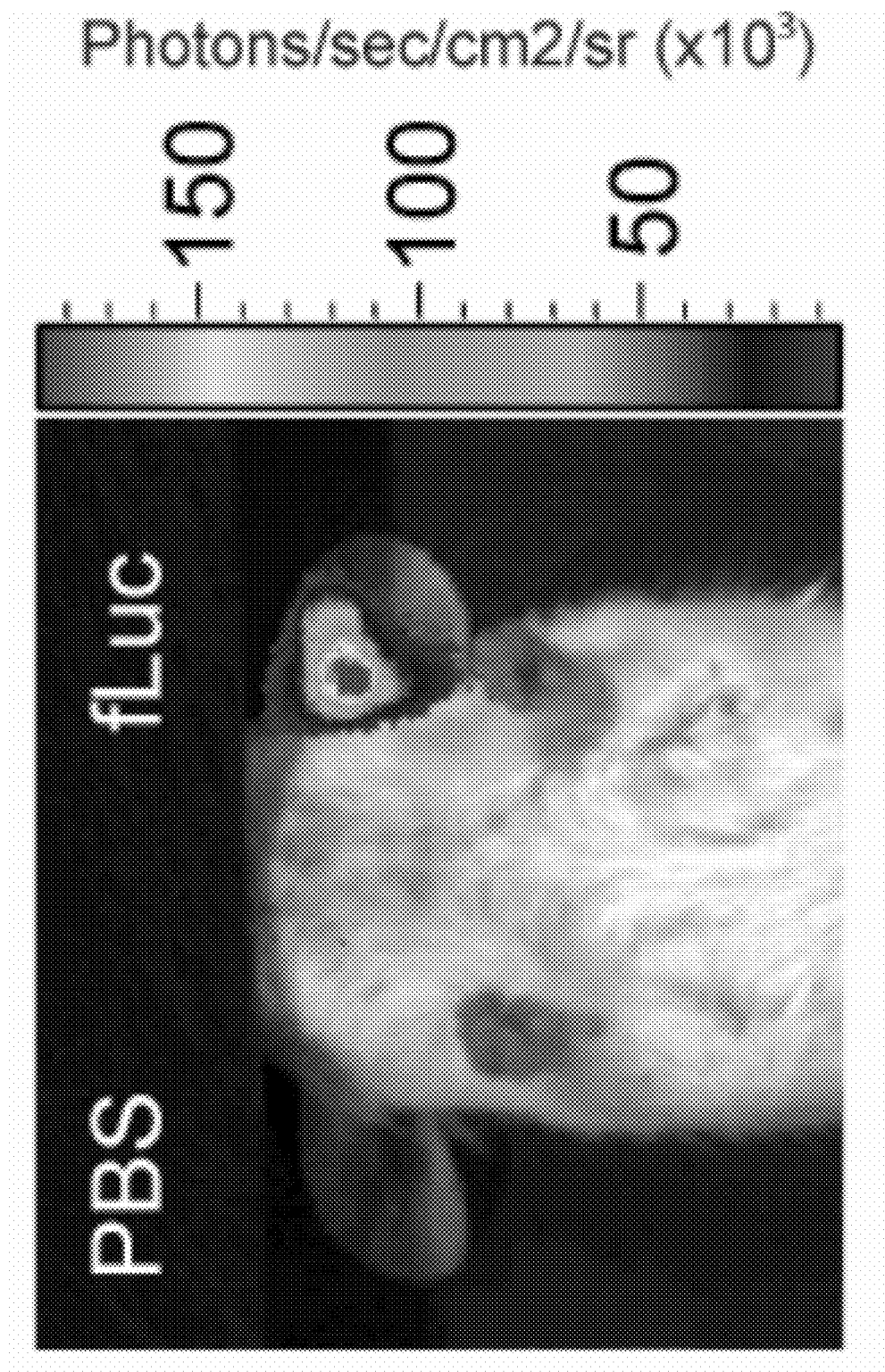
FIG. 6—Shows expression of fLuc reporter gene in mouse ear and mouse footpad administered by a microneedle array transdermal delivery device. A. The ear on the right was "injected" with a needle array loaded with ~50 μL fLuc expression plasmid (10 mg/mL in PBS) per needle. The ear on the left was "injected" with the STMNA delivery device loaded with PBS only. Needles were inserted into the ear for 20 min. After 24 h, luciferase expression was determined following IP luciferin injection by whole animal imaging using the Xenogen IVIS200 in vivo system. B. Shows footpad delivery. Reproducibility of microneedle array-mediated delivery of fLuc reporter plasmid was assessed by treating multiple mice. Left footpads were treated with microneedle arrays (12 needles) loaded with luciferase expression plasmid. Luciferase expression is observed in the left footpads following IP administration of luciferin, while right footpads, which received microneedles loaded with PBS vehicle alone, do not.

The ear on the right was "injected" with a microneedle array transdermal delivery device loaded with ~50 nL fLuc expression plasmid (10 mg/mL in PBS) per needle. The left ear was "injected" with a microneedle array transdermal delivery device loaded with PBS only to act as a control. The microneedles were inserted into the ear for 20 min. After 24 h, luciferase expression was determined following IP luciferin injection by whole animal imaging using the Xenogen IVIS200 in vivo system. FIG. 4 shows the expression of fLuc reporter gene in the mouse ear.

Example 15

Fabrication of a Composite Tip Microneedle Array

A microneedle array was fabricated following a procedure similar to that of Example 1, omitting step number 7, but otherwise performing the procedure to step number 8, but not continuing to step number 9. The microneedles were then momentarily contacted to a solution of approximately 0.1% gentian violet in 2% aqueous carboxymethylcellulose, by positioning the entire array of needle tips to press into an approximately 500 μm film of the gentian violet solution spread on a supporting substrate parallel to the substrate. Withdrawing the needles was observed to form smaller "needles upon needles" of the gentian violet solution. Upon drying as in step 9 of Example 1, these needles were observed to be of comparable sharpness and rigidity to the needles of Example 1, and would be expected to have different tip solubility characteristics. Any of the exemplary polymers presented above are believed to be suitable for forming such composite tips, which are expected to show various solubility behaviors under conditions of use.

Example 16

Manufacture of Microneedle

A polymer coated substrate is contacted with a series of pins and pins are allowed to remain in the polymer coating for a period of about 5 seconds while a a heated air (35° C.) is flowed across the substrate at a rate of about 1.0 m/s. The pins are then retrated from the substrate at a rate of 5 mm/s to a distance of about 1 cm. About halfway through the retraction (approximately 10 seconds) an additional airflow is introduced having a temperature of about 50° C. and a rate of about 2.0 m/s.

It is to be understood that the above-described methods, formulations, and experiments are only illustrative of preferred embodiments of the present invention. Numerous modifications and alternative arrangements may be devised by those skilled in the art without departing from the spirit and scope of the present invention and the appended claims are intended to cover such modifications and arrangements.

Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:
1. A transdermal delivery device, comprising:
 a polymer base layer having microneedles projecting from a surface thereof, wherein the microneedles are compositionally homogenous with the polymer base layer, and wherein the microneedles of the transdermal delivery device are configured to be left in a skin surface of a subject to provide sustained delivery of an active agent even after removal of the polymer base layer, and wherein the polymer of the polymer base layer and the microneedles is polyvinyl alcohol.

2. The transdermal delivery device of claim 1, wherein the microneedles are hollow.

3. The transdermal delivery device of claim 2, wherein the microneedles contain an active agent.

4. The transdermal delivery device of claim 1, wherein the polymer base layer has active agent included therein.

5. The transdermal delivery device of claim 1, wherein the microneedles have a length of from about 10 μm to about 10000 μm.

6. The transdermal delivery device of claim 1, wherein the polymer base layer is attached to a backing layer.

7. The transdermal delivery device of claim 1, wherein the transdermal delivery device is a transdermal patch.

* * * * *